United States Patent
Nakanishi et al.

(10) Patent No.: US 6,531,060 B1
(45) Date of Patent: Mar. 11, 2003

(54) CAPILLARY COLUMN INCLUDING POROUS SILICA GEL HAVING CONTINUOUS THROUGHPORES AND MESOPORES

(75) Inventors: Kazuki Nakanishi, Kyoto (JP); Naohiro Soga, Kobe (JP); Hiroyoshi Minakuchi, Kyoto (JP)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/646,921

(22) PCT Filed: Mar. 29, 1999

(86) PCT No.: PCT/EP99/02129

§ 371 (c)(1),
(2), (4) Date: Sep. 25, 2000

(87) PCT Pub. No.: WO99/50654

PCT Pub. Date: Oct. 7, 1999

(30) Foreign Application Priority Data

Apr. 1, 1998 (JP) .................................... 10-88627

(51) Int. Cl.⁷ .................... B01D 15/08; B01D 53/14; C03C 11/00; G01N 30/60
(52) U.S. Cl. .................... 210/198.2; 210/502.1; 96/101; 422/70; 422/89
(58) Field of Search .................... 210/656, 198.2, 210/263, 502.1; 95/82, 88; 96/101; 73/19.02, 61.52, 61.53; 722/70, 89

(56) References Cited

U.S. PATENT DOCUMENTS

| | | | |
|---|---|---|---|
| 3,417,028 A | * | 12/1968 | Montogomery et al. |
| 3,782,075 A | * | 1/1974 | Kirkland |
| 3,855,172 A | * | 12/1974 | Iler et al. |
| 4,137,161 A | * | 1/1979 | Shimada et al. |
| 4,727,209 A | | 2/1988 | Chao |
| 5,176,832 A | * | 1/1993 | Dorta et al. |
| 5,192,351 A | | 3/1993 | Mathur et al. |
| 5,242,471 A | * | 9/1993 | Markham et al. |
| 5,624,875 A | * | 4/1997 | Nakanishi et al. |
| 5,637,135 A | * | 6/1997 | Ottenstein et al. |
| 5,647,979 A | | 7/1997 | Liao et al. |
| 5,728,457 A | * | 3/1998 | Frechet et al. |
| 5,759,234 A | * | 6/1998 | Munari et al. |
| 5,869,152 A | | 2/1999 | Colon |
| 5,875,564 A | | 3/1999 | Kirkbir et al. |
| 6,054,052 A | * | 4/2000 | Dhingra et al. |
| 6,207,098 B1 | * | 3/2001 | Nakanishi et al. |

FOREIGN PATENT DOCUMENTS

| | | | |
|---|---|---|---|
| EP | 0809108 | * | 11/1997 |
| WO | WO 95/03256 | * | 2/1995 |
| WO | WO 98/29350 | | 7/1998 |
| WO | WO 99/30147 | * | 6/1999 |

OTHER PUBLICATIONS

Crister Ericson et al., "Preparation of continuous beds for electrochromatography and reversed–phase liquid chromatography of low–molecular–mass compounds", Apr. 1997, Journal of Chromatography A, vol. 767, pp. 33–41.*

* cited by examiner

Primary Examiner—David A. Simmons
Assistant Examiner—Fred Prince
(74) Attorney, Agent, or Firm—Millen, White, Zelano & Branigan, P.C.

(57) ABSTRACT

A capillary column comprising a capillary of which the inner diameter is less than 1000 μm and a continuous porous silica gel which uniformly fills the capillary, said silica gel containing both continuous through pores having diameters ranging from 0.5–5 μm and mesopores having diameters ranging from 2–50 nm.

11 Claims, 18 Drawing Sheets

Figure 1:
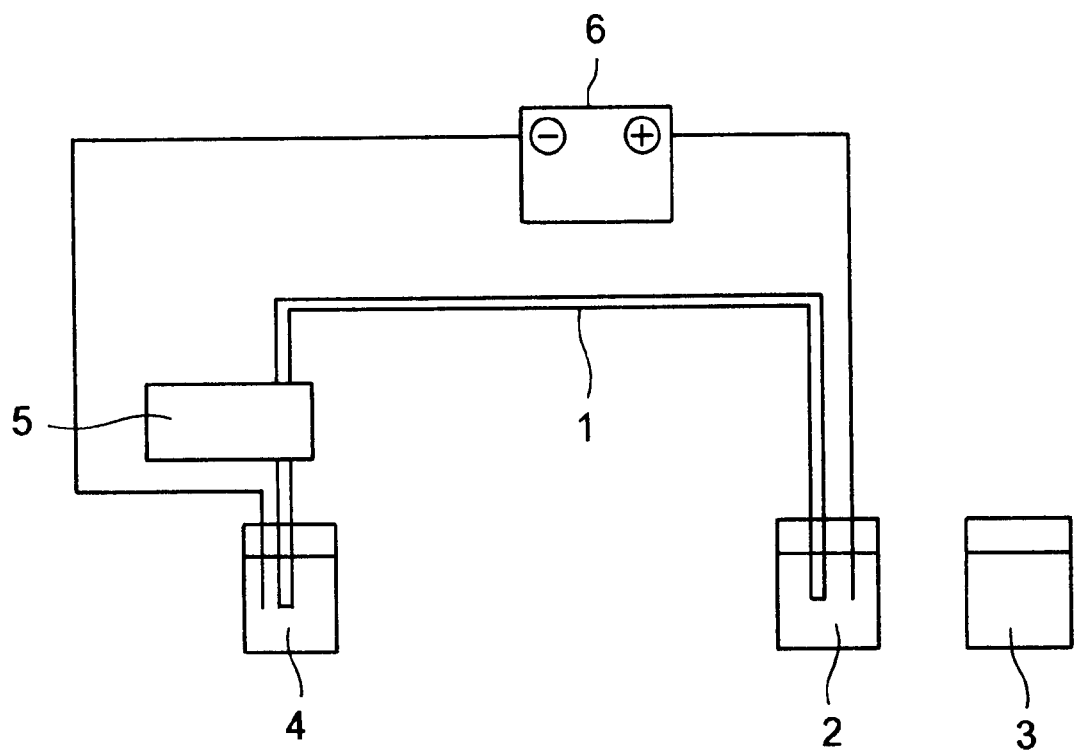

CAPILLARY COLUMN INCLUDING POROUS SILICA GEL HAVING CONTINUOUS THROUGHPORES AND MESOPORES

The present invention concerns a capillary column which can be used in a liquid chromatograph, a gas chromatograph, an electrophoretic equipment, a solid state extraction apparatus and so forth.

In the conventional liquid chromatography, smaller column volume is favored for reducing the consumption of mobile phase. For the purpose of maintaining a high analytical performance, the column diameter instead of column length is reduced. A column with reduced diameter, called capillary column, is usually prepared by stuffing inorganic packing materials such as silica gels in a capillary by physical means.

The packing materials used in electrochromatography should carry electrostatic charge on their surfaces. Accordingly, inorganic porous materials which retain stable negative charges in a neutral pH condition, especially silica gels, are widely used.

The sol-gel method is one of liquid phase reaction paths to produce inorganic porous materials, especially silica gels. The sol-gel method denotes widespread processes in which polymerizable low molecular weight species are first generated, and through polymerization reactions, aggregated or polymerized materials are finally obtained. For example, the sol-gel method can be applied by hydrolyzing metal alkoxides, metal chlorides, metal salts or coordinated compounds which typically contain carboxyl or beta-diketone ligands.

Particle-packed capillary columns for electrochromatography have been prepared by physically packing inorganic particulate materials into a capillary. In order to avoid the change in the packing state of the particles due to their motion in the capillary, the both ends of a capillary are fitted with the parts called "frit" with relatively low porosity.

Particle-packed capillary columns are disadvantageous in the points that: (a) the packing procedure is complicated and time-consuming. (b) the reproducibility of the packing state, and correspondingly that of an excellent analytical performance, is poor. (c) Since the homogeneous packing of an entire capillary becomes increasingly difficult as the column length increases, an improvement of the analytical performance by increasing the total column length is not practical.

In addition, particle-packed capillary columns equipped with the frits at both ends frequently cause bubbling at the space between the frit and packed-beds, thus require additional pressurization for normal chromatographic operation.

In spite of the fact that the analytical performance of a capillary column is governed by its inner porous structure directly related to the packing state of the particles, no particle-packing method which produces the stable and reproducible packing state has been established.

Further, although smaller particle size is required for acclerated separation, the applied pressure becomes high for a capillary packed with smaller particles, which makes it difficult for practical uses.

The present inventors have found that: A capillary column which exhibits homogeneous and continuous double pore structure through the whole length of the capillary can be obtained by the processes of; 1) to form a three-dimensional co-continuous network consisting of an inorganic gel phase and a solvent phase both having average domain size of larger than 100 nm via a sol-gel process from a solution precursor containing a thermally decomposable component in a capillary with the inner diameter of less than 1 mm, 2) to modify the nanometer-range microstructures into that consisting of sharply distributed mesopores smaller than 50 nm in diameter by heating the wet gel to decompose said thermally decomposable component, 3) to dry and heat-treat the gel to obtain completely inorganic porous material. EP 0 710 219 discloses in detail procedures suitable for preparing porous silica materials with defined macro and meso pores. WO 98/29 350 discloses the use of thermolysable compounds to modify the pore structure of micropores. EP 98/08 295 is concerned with processes to make inorganic porous materials in a narrow bored column.

The present invention has been developed based on the above knowledge. The invention provides capillary columns with a well-defined and highly reproducible internal pore structure through the whole length of the capillary. Also the capillary consumes less mobile phase, requires lower column pressure, and provides an excellent analytical performance.

Short explanations of figures:

FIG. 1: Schematic diagram of an electrochromatograph

Figure 2:
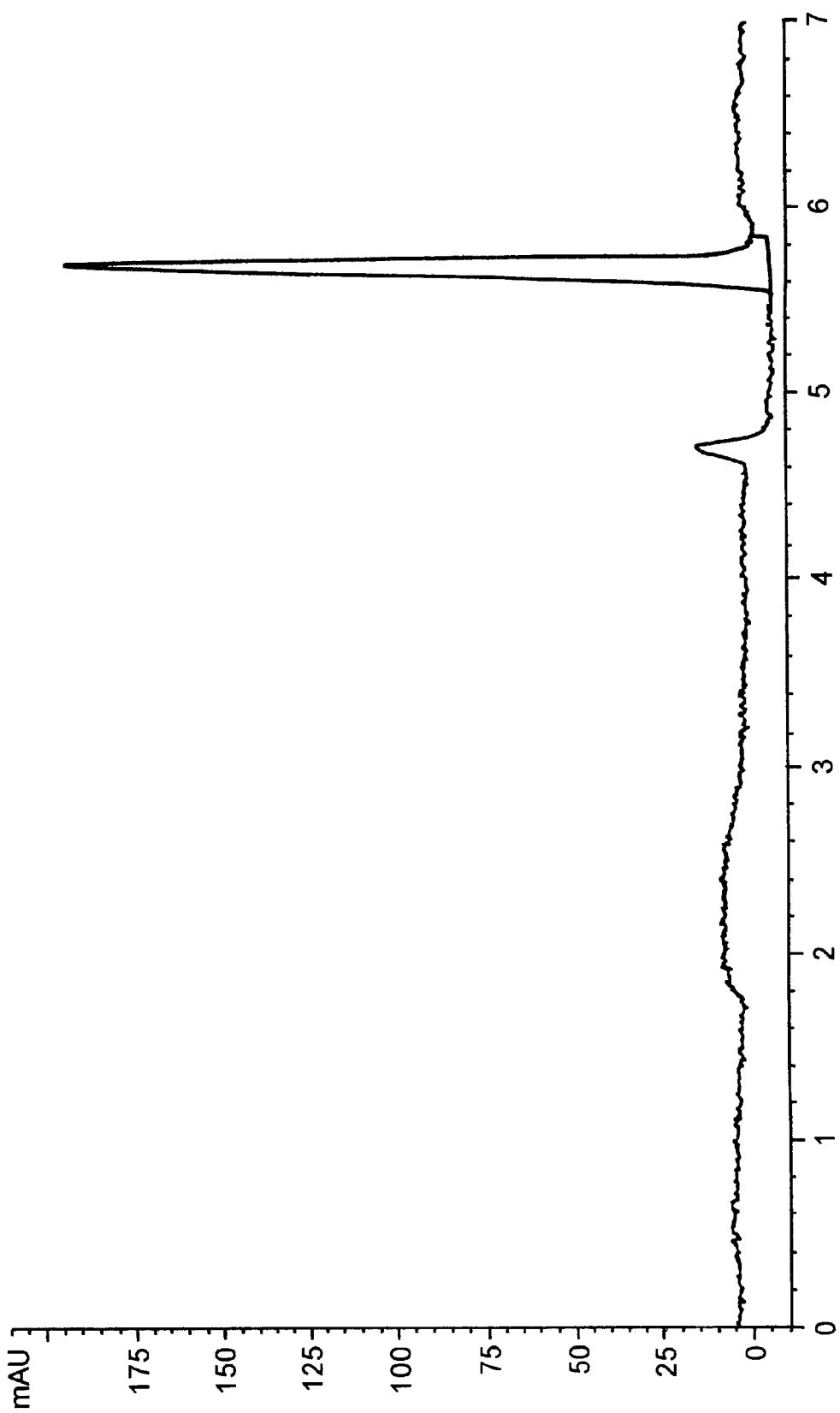

FIG. 2: A chromatogram of thiourea analyzed with the applied voltage of 15 kV.

Figure 3:
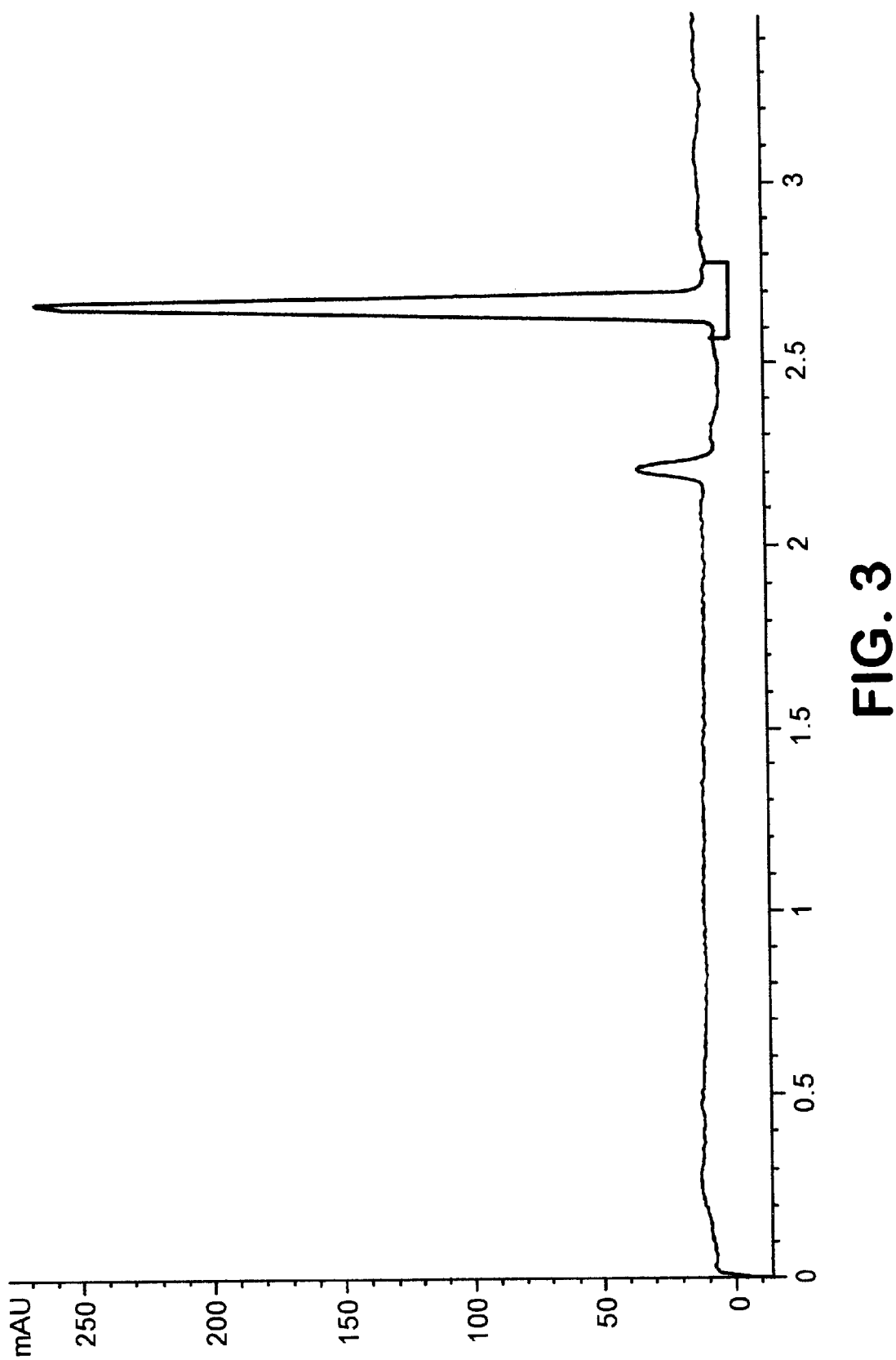

FIG. 3: A chromatogram of thiourea analyzed with the applied voltage of 25 kV.

Figure 4:
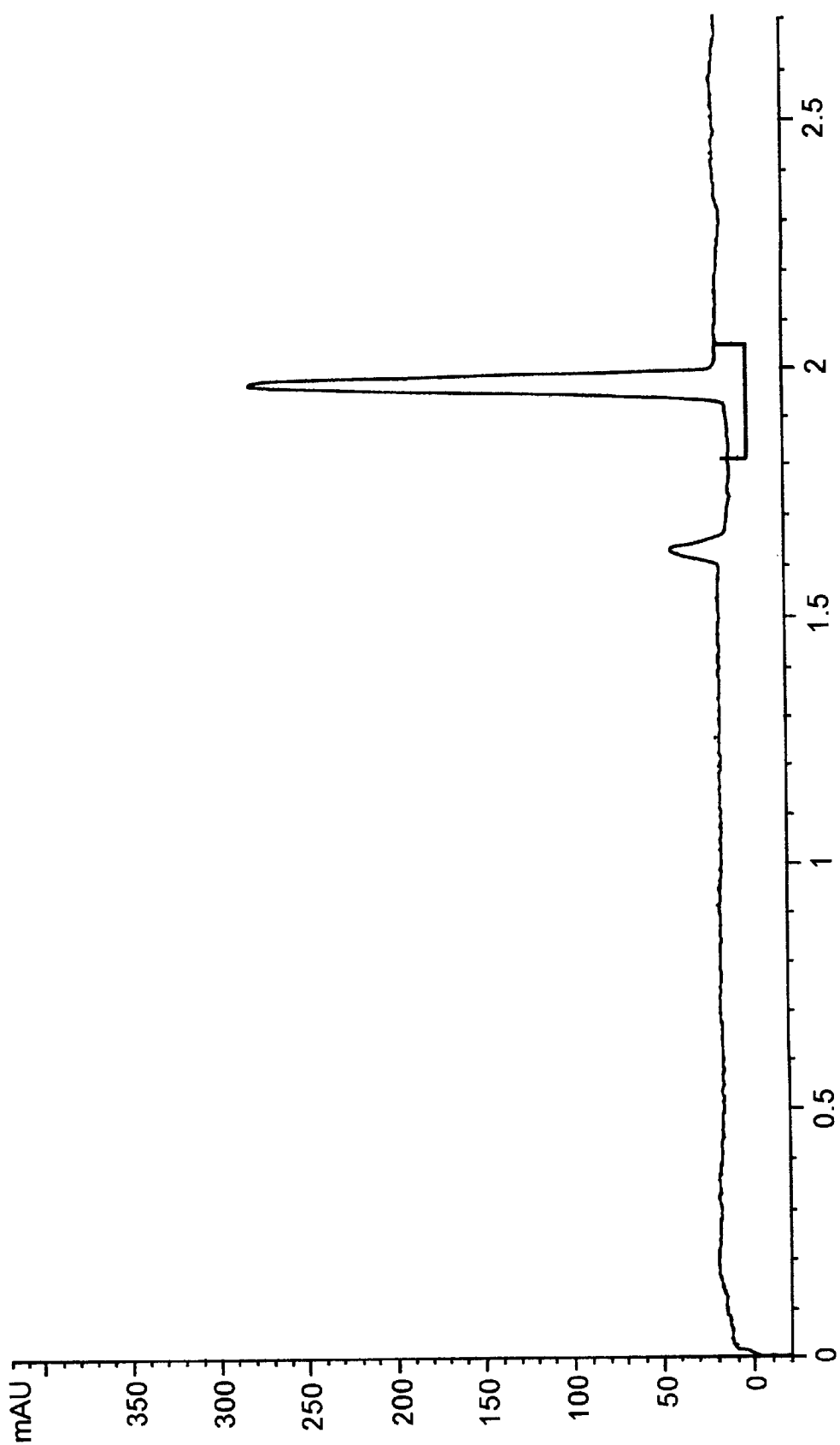

FIG. 4: A chromatogram of thiourea analyzed with the applied voltage of 30 kV.

Figure 5:
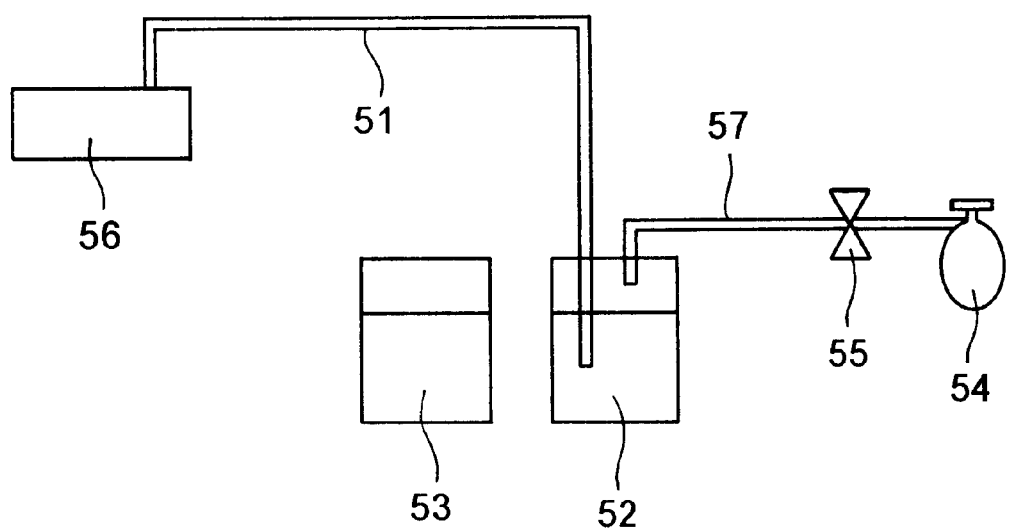

FIG. 5: Schematic diagram of a chromatograph with gas pressurizing device.

Figure 6:
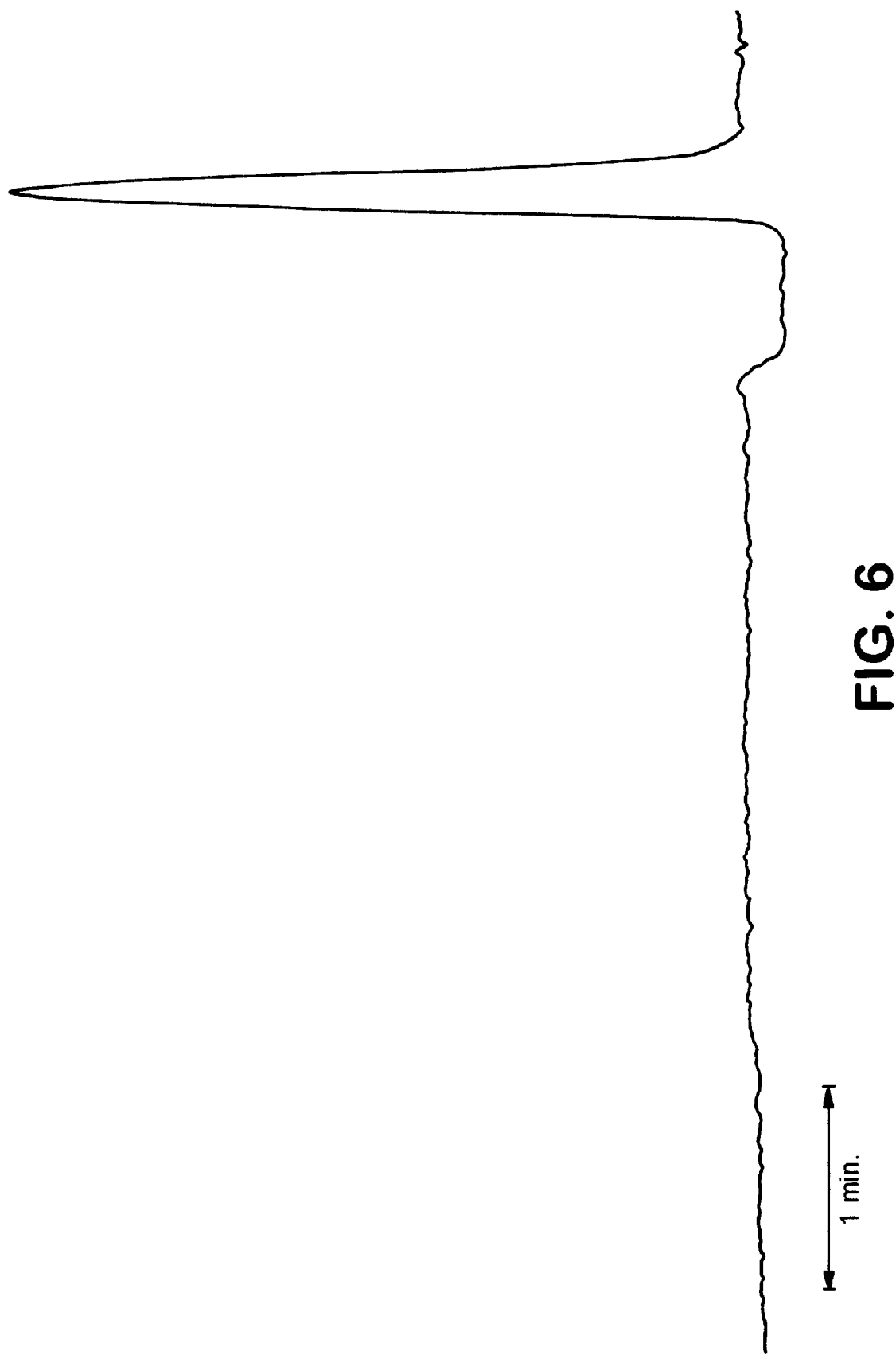

FIG. 6: A chromatogram of thiourea with the applied pressure of 1 kg/cm$^2$.

Figure 7:
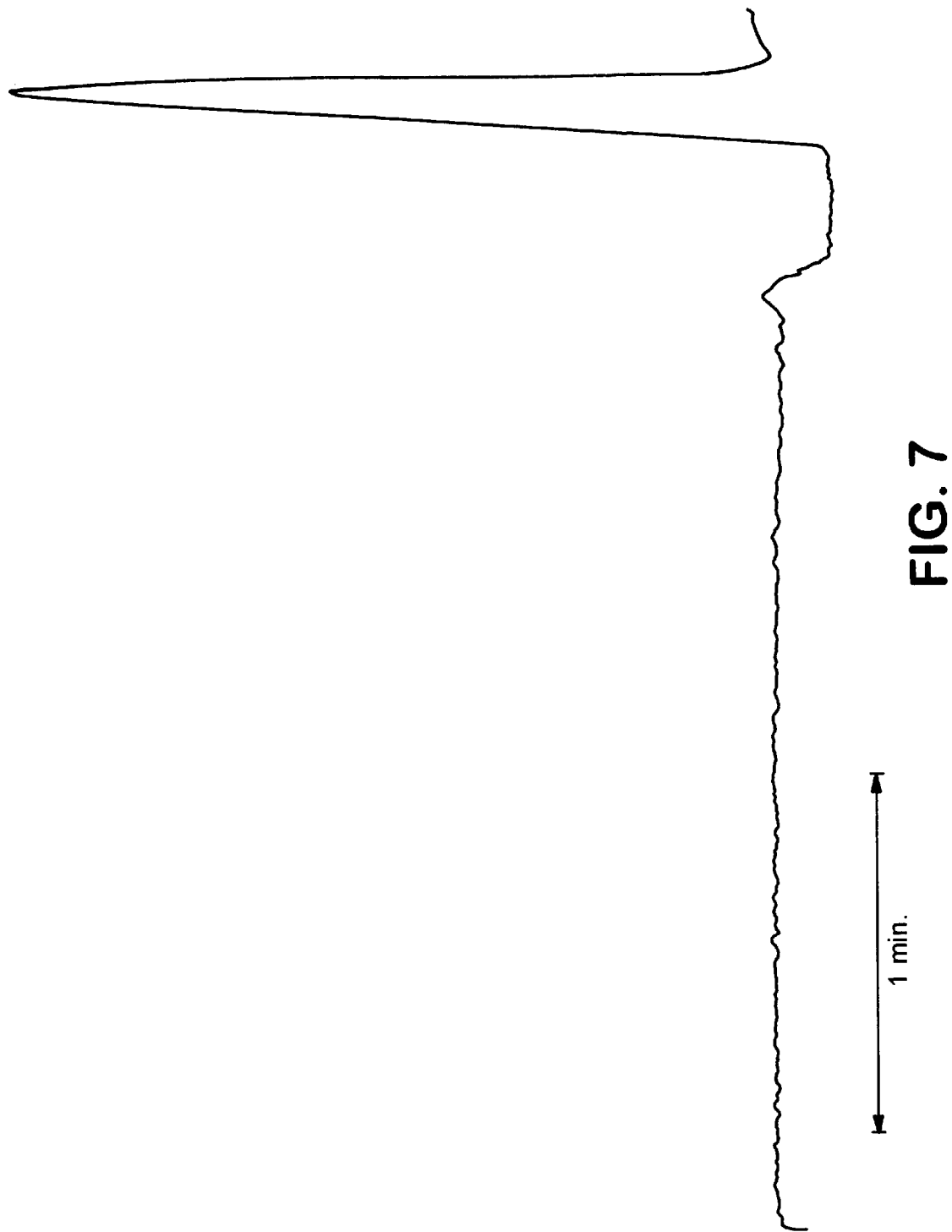

FIG. 7: A chromatogram of thiourea with the applied pressure of 2 kg/cm$^2$.

Figure 8:
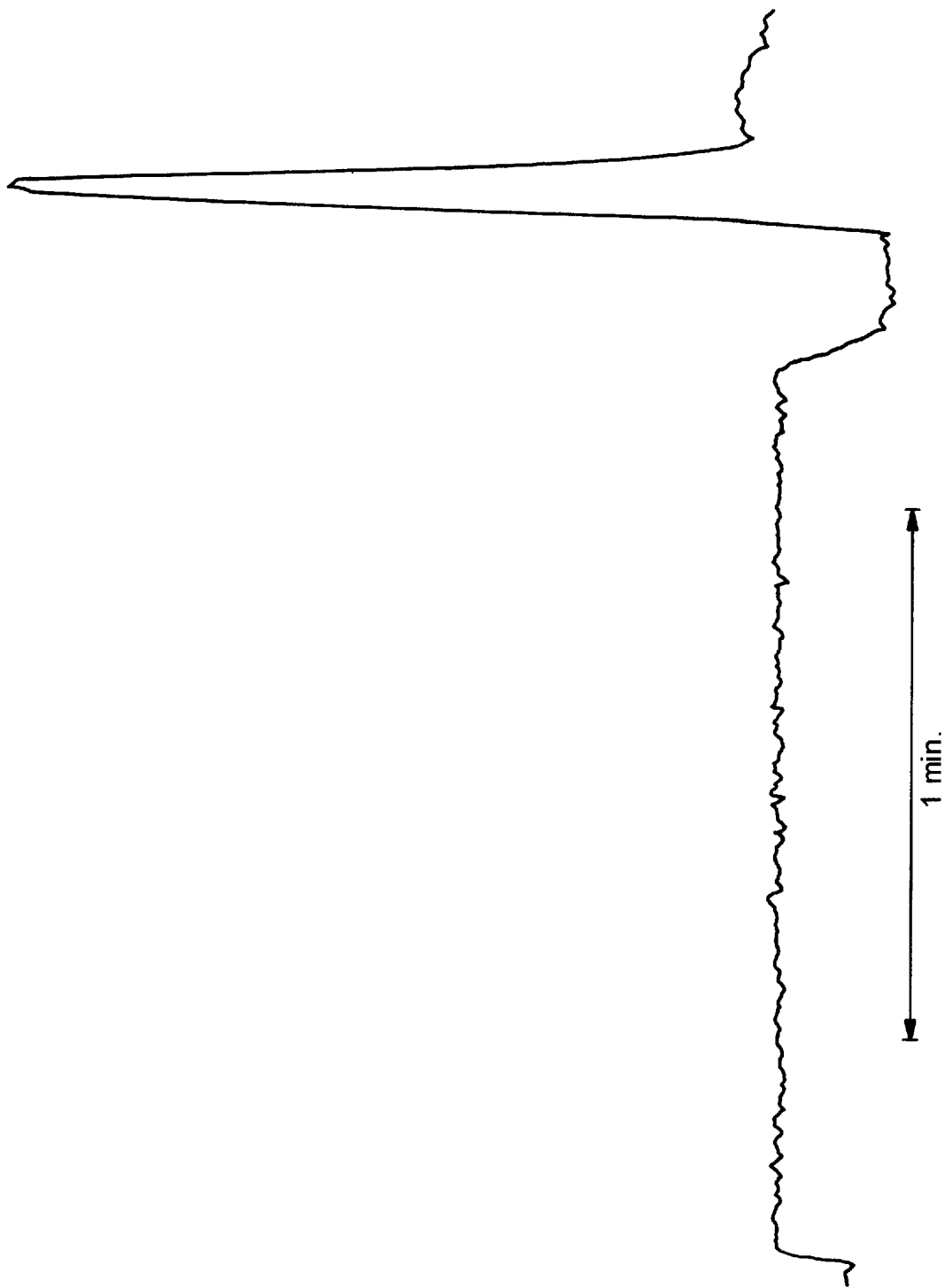

FIG. 8: A chromatogram of thiourea with the applied pressure of 3 kg/cm$^2$.

Figure 9:
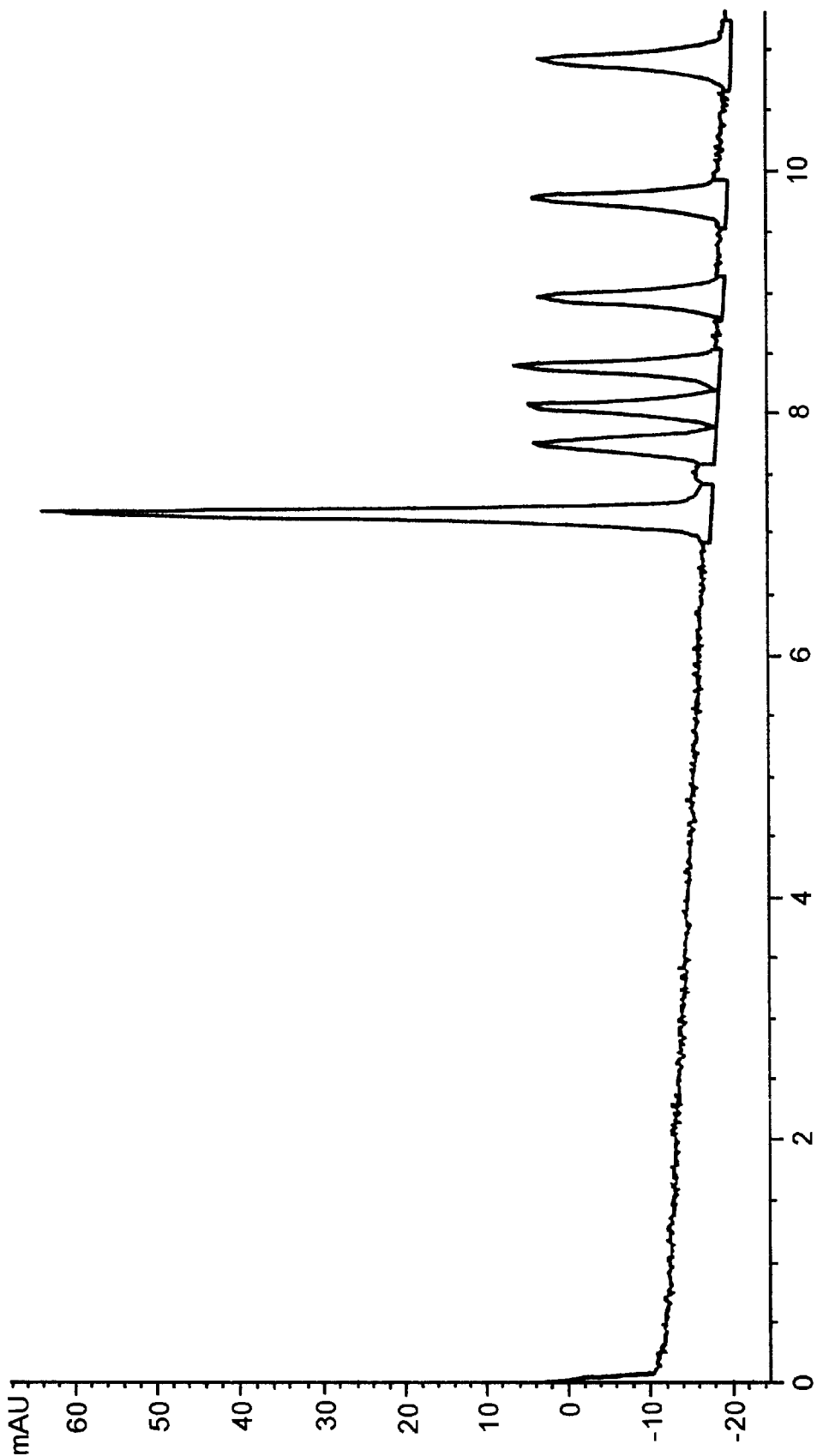

FIG. 9: A chromatogram of alkylbenzenes with the ODS column and applied voltage of 20 kV.

Figure 10:
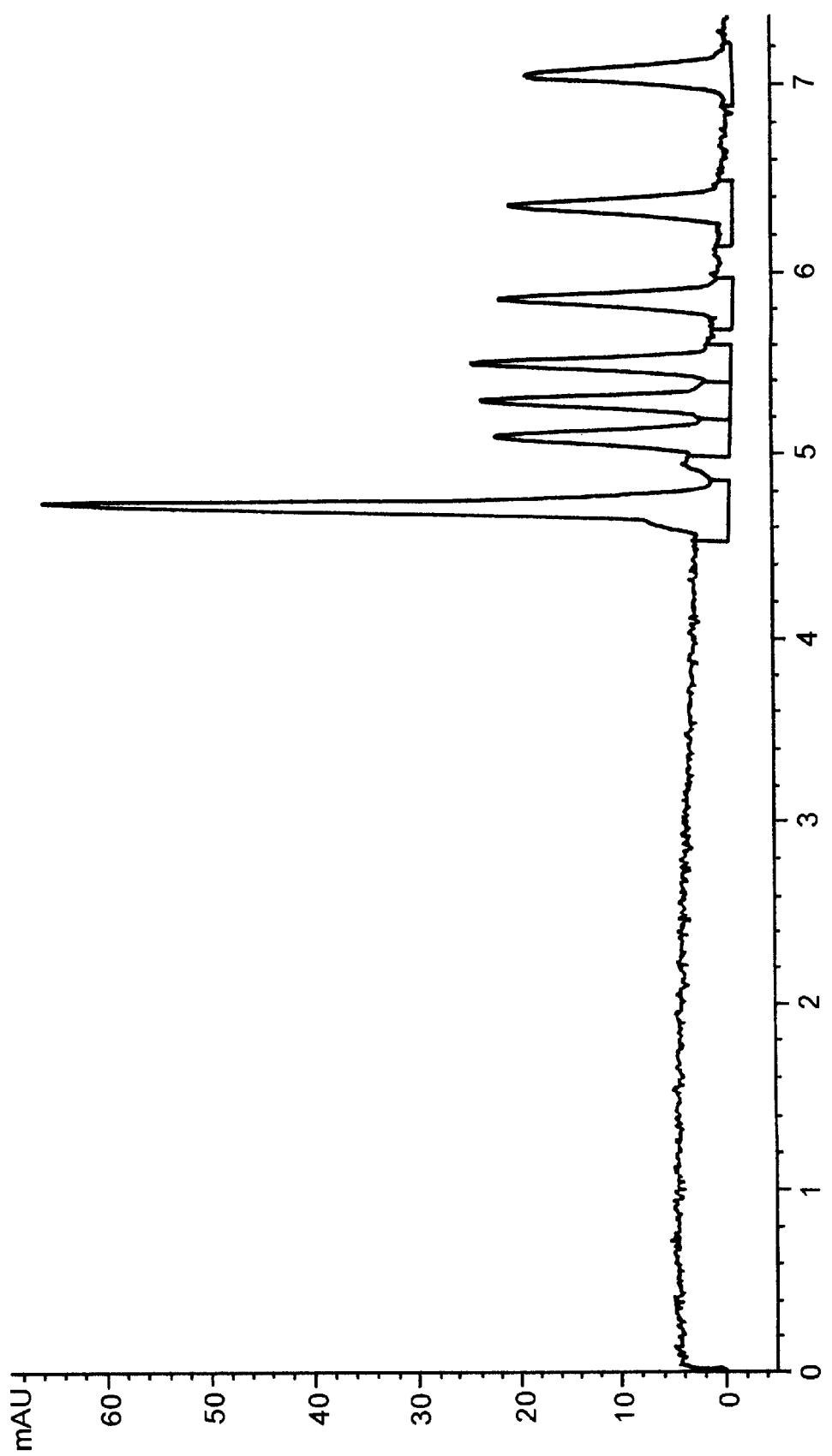

FIG. 10: A chromatogram of alkylbenzenes with the ODS column and applied voltage of 30 kV.

Figure 11:
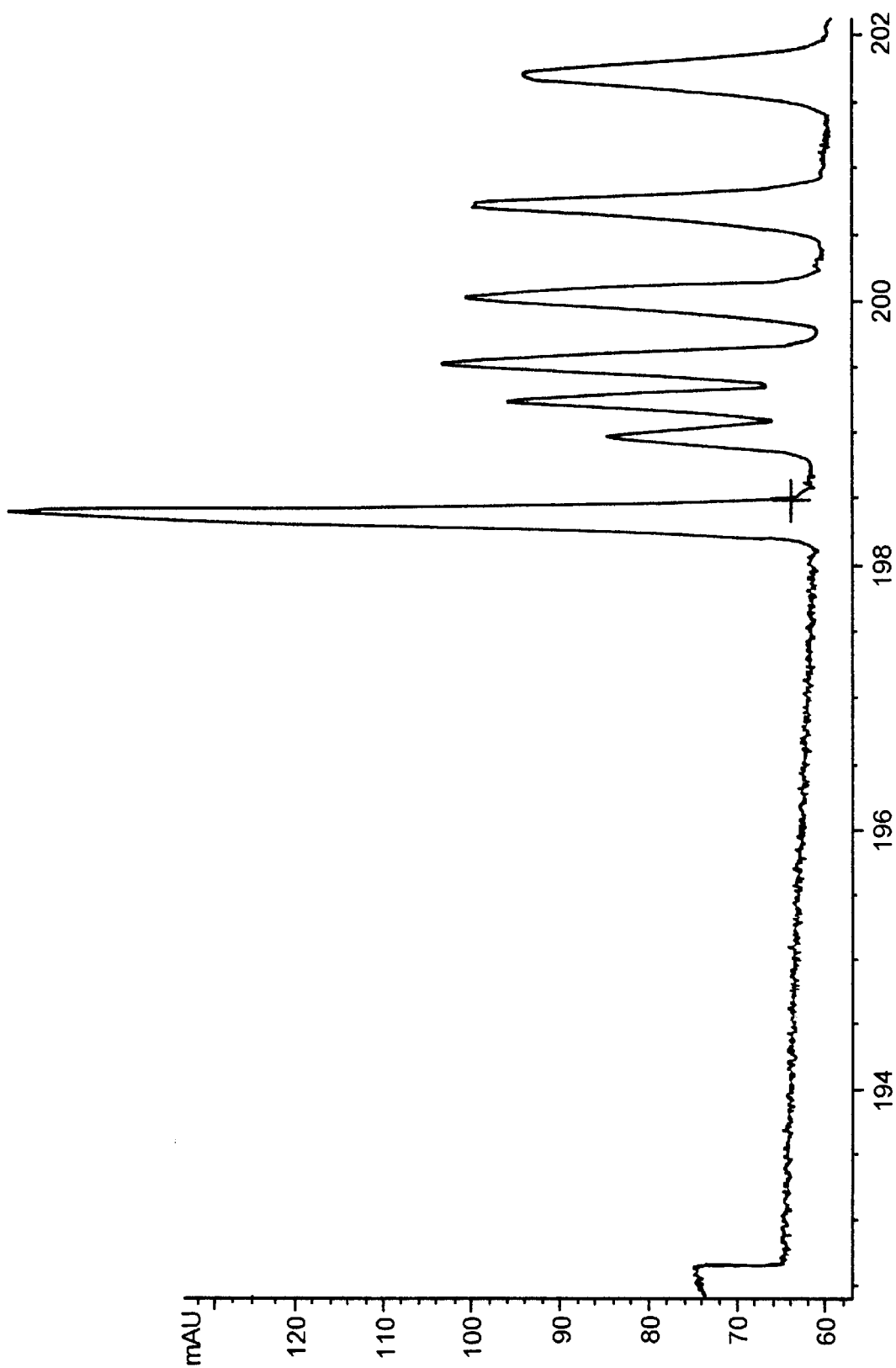

FIG. 11: A chromatogram of alkylbenzenes with the ODS column and applied pressure of 1 kg/cm.

Figure 12:
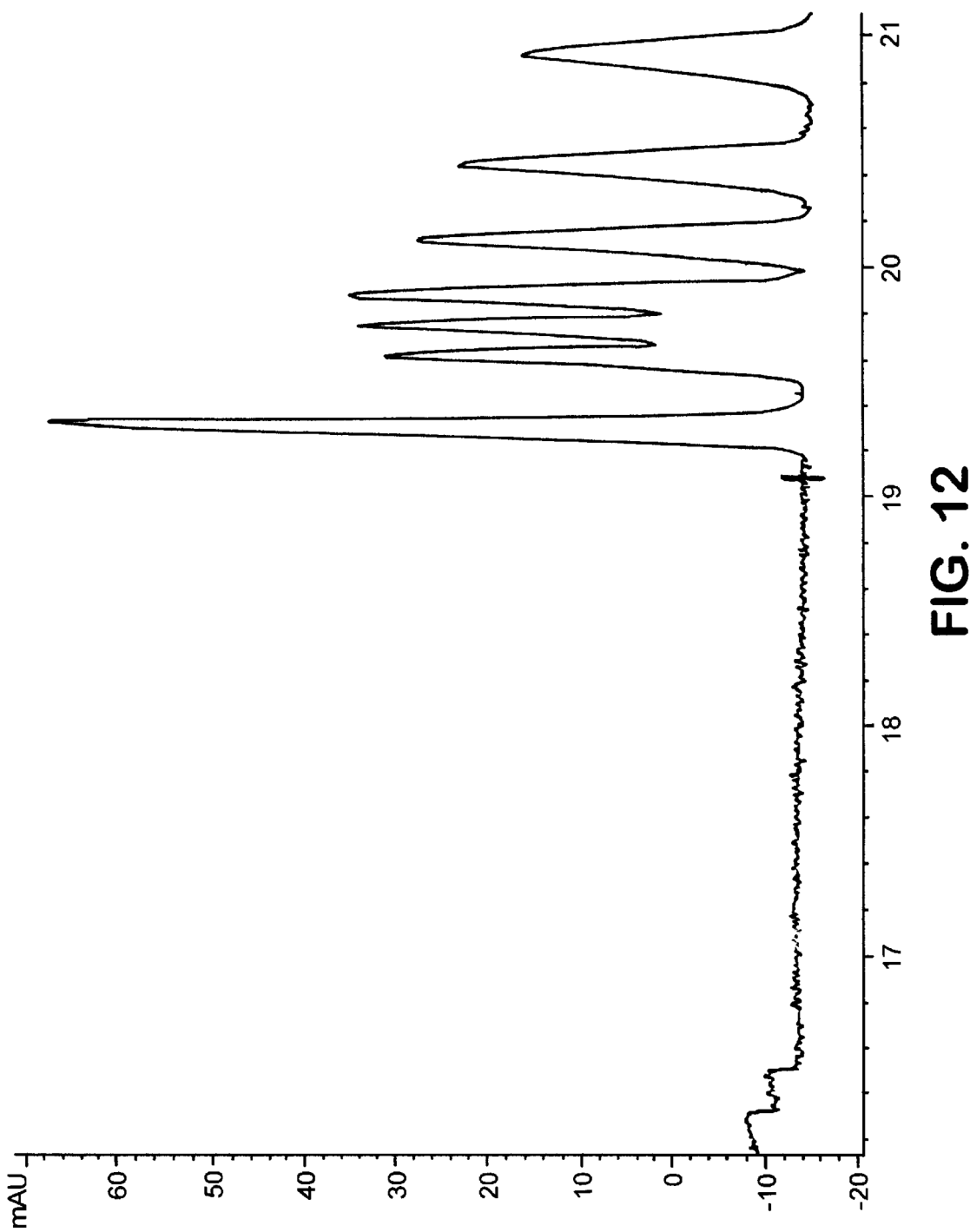

FIG. 12: A chromatogram of alkylbenzenes with the ODS column and applied pressure of 2 kg/cm$^2$.

Figure 13:
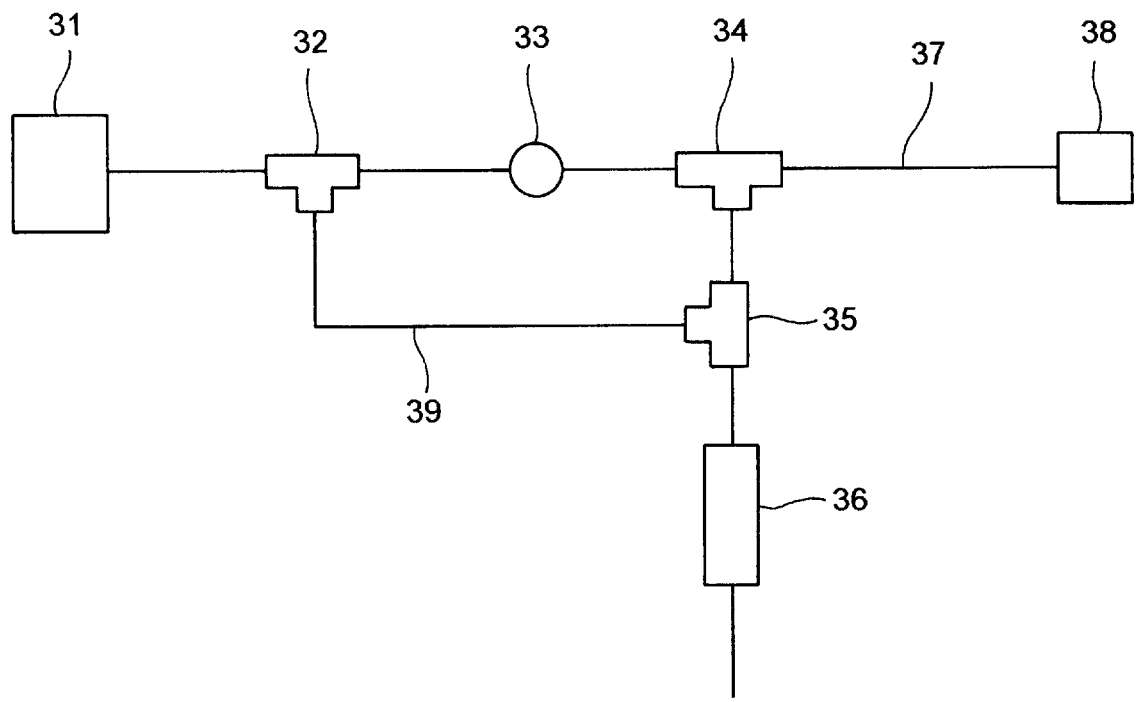

FIG. 13: Schematic diagram of a chromatograph with the split device.

Figure 14:
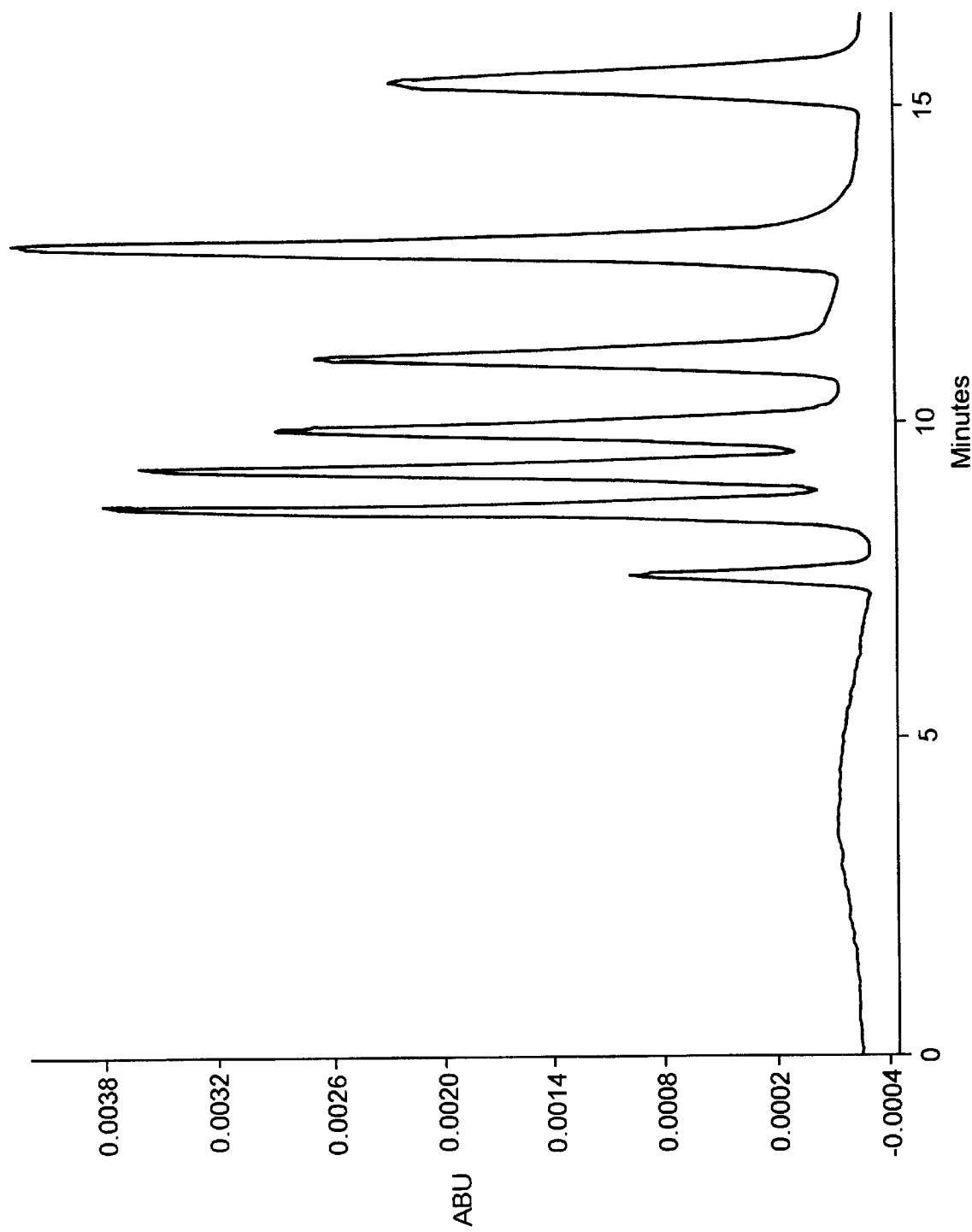

FIG. 14: A chromatogram of alkylbenzenes with the mobile phase velocity of 0.1 ml/min.

Figure 15:
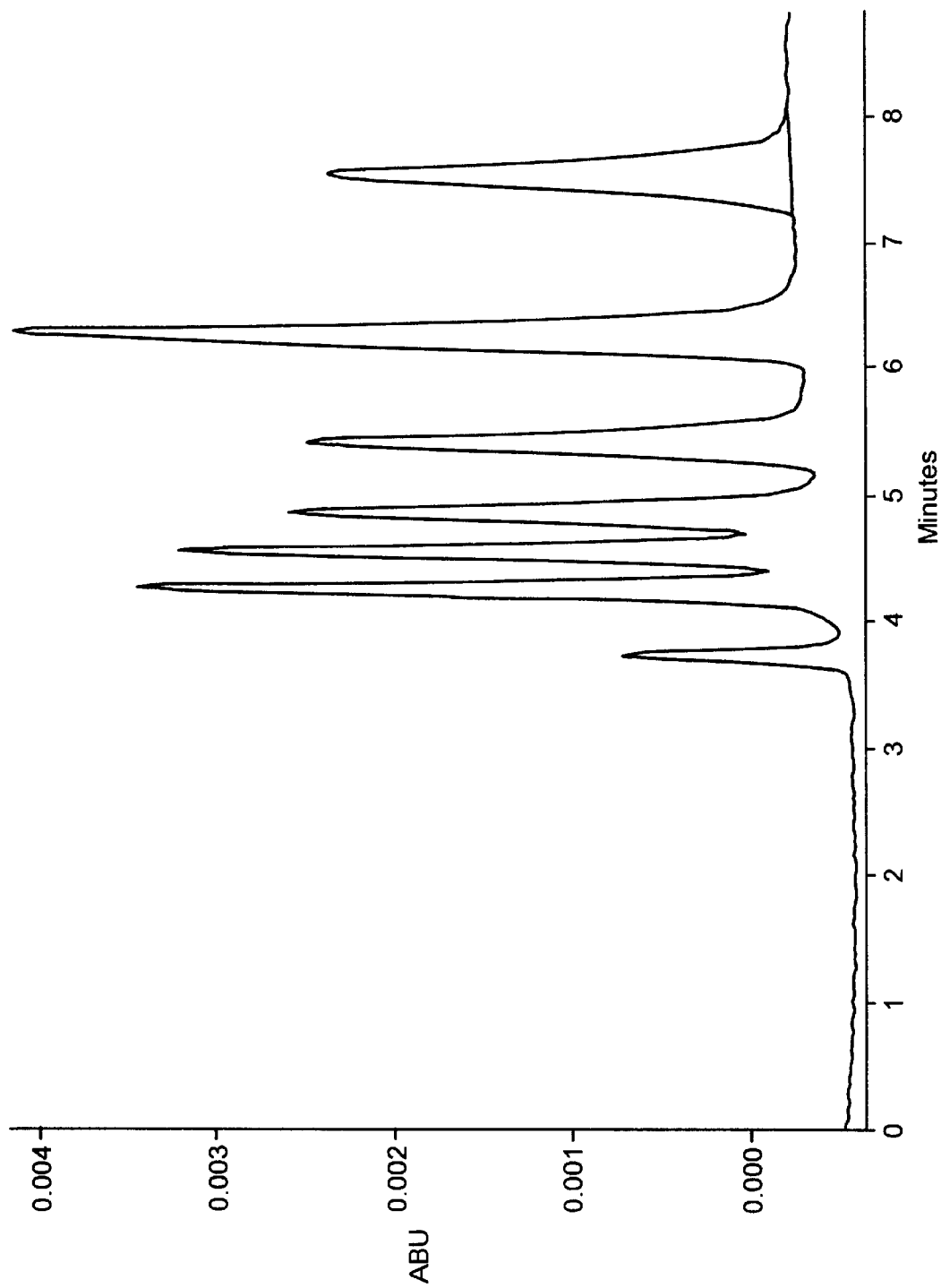

FIG. 15: A chromatogram of alkylbenzenes with the mobile phase velocity of 0.2 ml/min.

Figure 16:
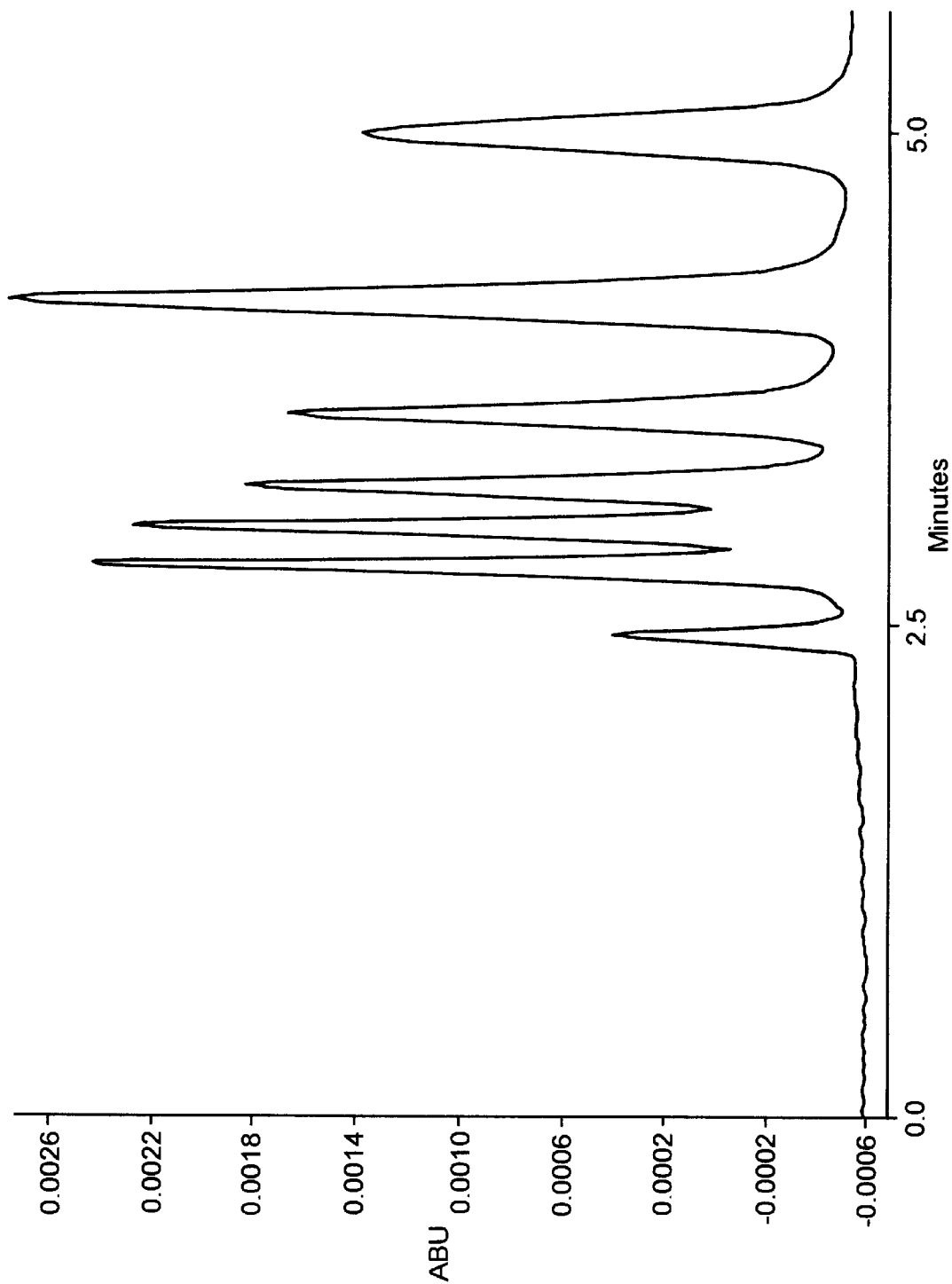

FIG. 16: A chromatogram of alkylbenzenes with the mobile phase velocity of 0.3 ml/min.

Figure 17:
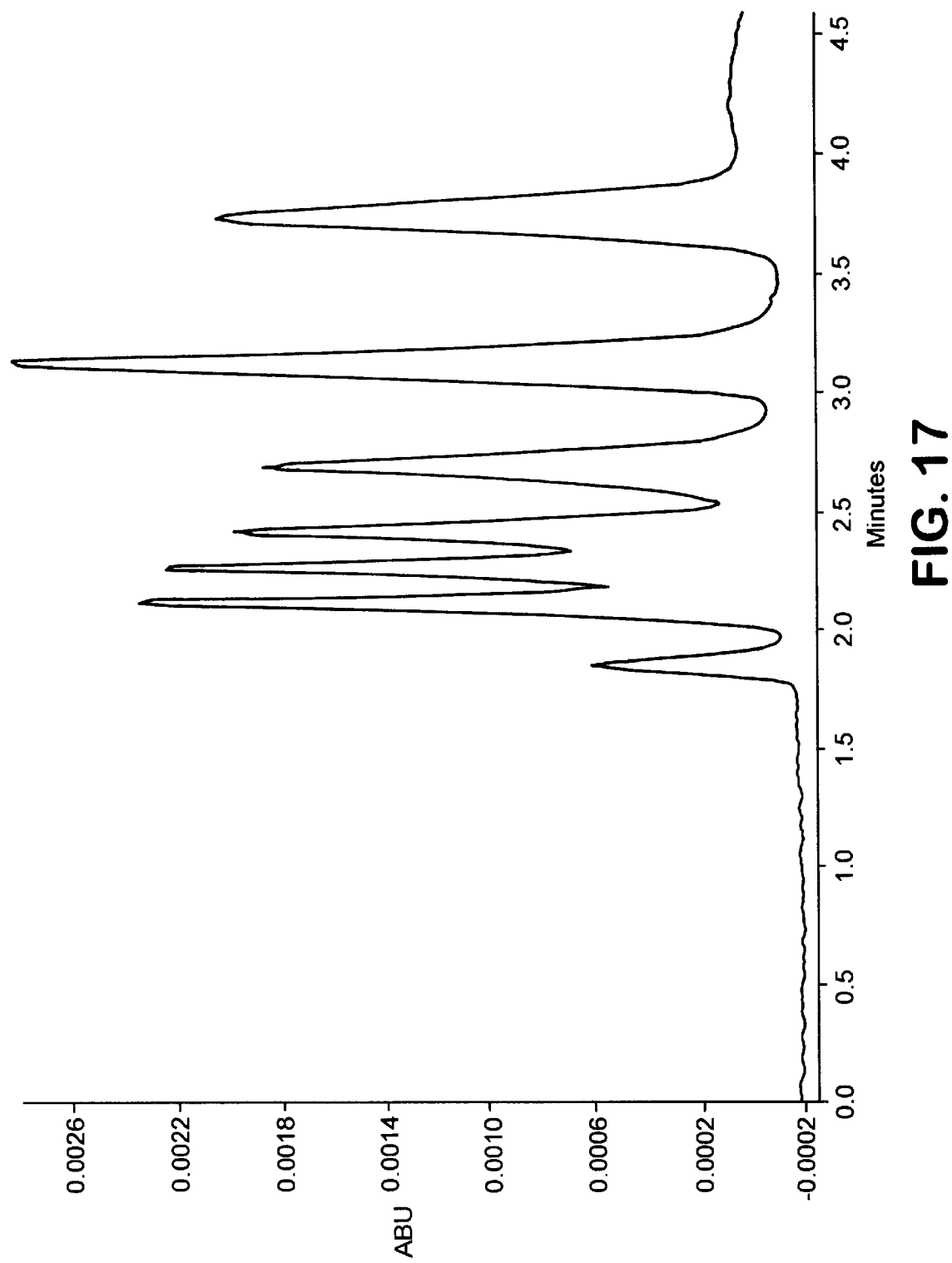

FIG. 17: A chromatogram of alkylbenzenes with the mobile phase velocity of 0.4 ml/min.

Figure 18:
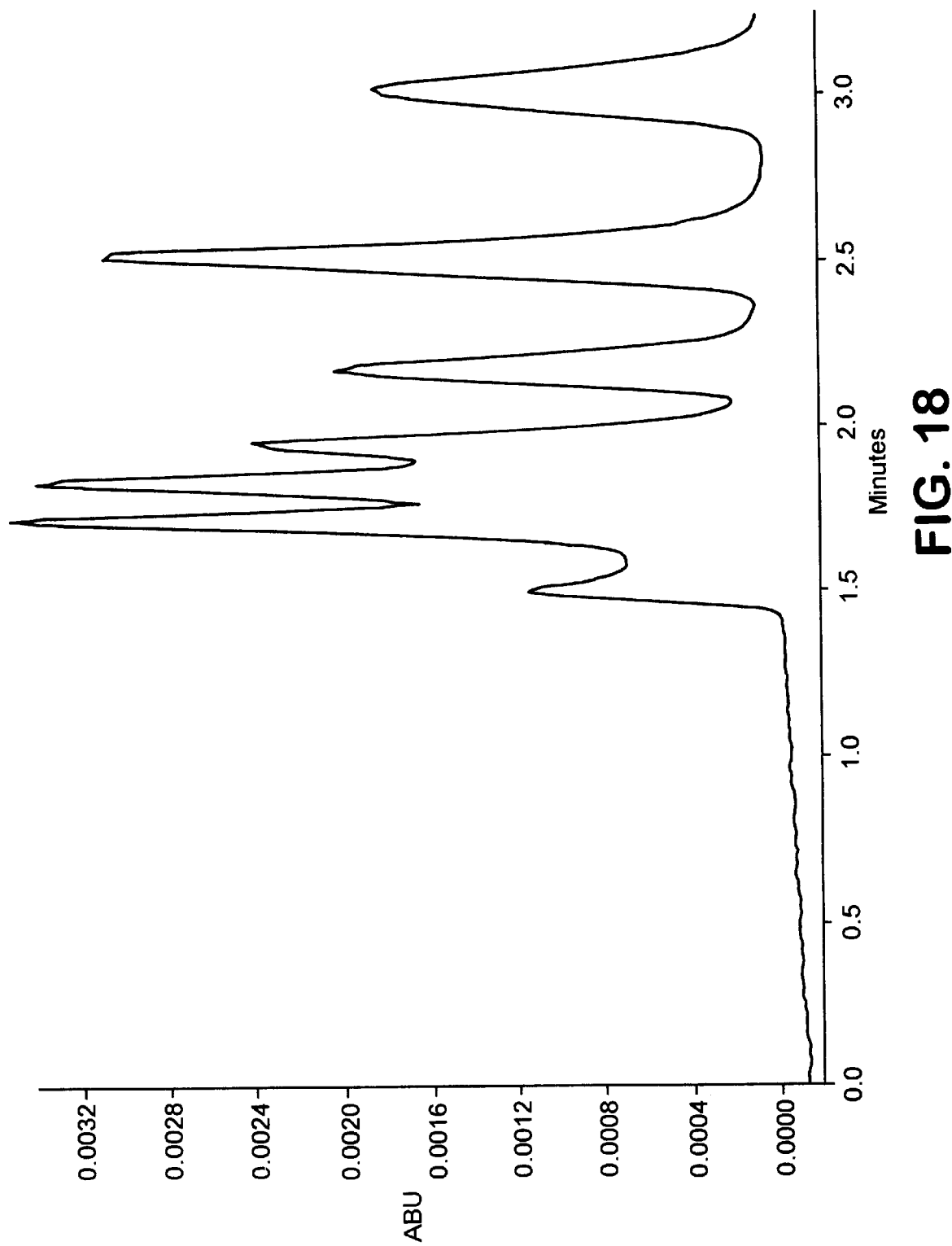

FIG. 18: A chromatogram of alkylbenzenes with the mobile phase velocity of 0.5 ml/min.

Details regarding these figures are given in the examples.

The present invention concerns a capillary column which consists of a capillary of which diameter is less than 1000 μm and continuous porous silica gel which uniformly fills said capillary. Said silica gel has double-pore structure which includes both continuous through pores of which diameter is 0.5–5 μm and mesopores of which diameter is 2–50 nm. The present invention further concerns the use of said capillary columns in separating equipment and separating equipment comprising said capillary columns. Examples of separating equipment in which said capillary columns can be used are liquid chromatographs, gas chromatographs, and electrophoresis equipment.

One means of the present invention to attain said object is characterized by previously dissolving a thermally decomposable compound in a reaction solution, forming, from said reaction solution through its sol-gel conversion in a capillary with the inner diameter of less than 1000 μm, a gel that comprises a solvent-rich phase containing three-dimensionally networked open pores having a mean pore diameter of not smaller than 100 nano-meters and an inorganic substance-rich skeleton phase containing particles each having fine pores on their surface, then heating the wet gel to thermolyze said thermally decomposable compound existing in the reaction system, and thereafter drying and heating the gel.

In one preferred embodiment of said means, silica $SiO_2$ is used as the inorganic substance while an amide compound, such as urea, capable of making the reaction system basic through its thermolysis is used as the thermally decomposable, low-molecular compound.

Another means of the present invention also to attain said object is characterized by dissolving a water-soluble polymer and a thermally decomposable compound in an aqueous acidic solution, adding thereto a metal compound having hydrolyzable functional groups to thereby hydrolyze said compound, solidifying the resulting product in a capillary with the inner diameter of less than 1000 μm, then heating the wet gel to thereby thermolyze the thermally decomposable low molecular compound existing in said gel, and thereafter drying and further heating the gel.

The substance to be added to the starting metal alkoxide is one having the function of inducing both sol-gel conversion and phase separation at the same time. Using this, the reaction system is separated into a solvent-rich phase and a skeleton phase, which is being gelled. As the substance of that type, a polymer soluble in solvents, such as sodium- or potassium-salts of polystyrene sulfonate, poly(acrylic acid), polyethylene oxide, polyvinyl pyrrolidone, polyethylene imine and polyallylamine is preferred. Other substances usable for this purpose are mixtures of formamide and polyalcohols; glycerol is the preferred poyalcohol for said purpose.

The metal alkoxide is preferably a silicon alkoxide, which may include, for example, tetramethoxysilane, tetraethoxysilane, methyltrimethoxysilane, ethyltrimethoxysilane and vinyl trimethoxysilane. However, these are not limitative. The metalic elements corresponds to those contained in the desired oxide phase can be Si, Ti, Zr or Al. Both alkoxides containing single or multiple kinds of metals can be used. The oligomers of the alkoxides, usually up to decamers, can be used as far as they dissolve or disperse homogeneously in the solvent alcohol.

The acidity of the aqueous solution used to hydrolyze the metal alkoxide is preferably stronger than 0.001 mol/L of mineral acid such as hydrochloric acid or nitric acid.

The capillary, made of fused silica for example, should have an inner diameter of less than 1000 μm, preferrably between 30 and 200 μm. The hydrolysis is conducted by homogeneously mixing the starting materials under the conditions of; temperature between 0 and 40° C., mixing time between 5 and 60 minutes. The phase separation and gelation is conducted under the conditions of; temperature between 40 and 80° C., reaction time between 0.5 and 5 hours. The hydrolysis and polycondensation follows the steps of 1) initially transparent solution becomes gradually opaque due to the phase separation into a gel phase and a pore-forming phase, 2) the whole solution loses fluidity and turns into gel. During the whole reaction steps the water-soluble polymer is molecularly dissolved in the solution and no effective precipitation occurs.

One embodiment of the present invention for producing a porous inorganic material, in which the pore structure of the porous inorganic material can be most effectively controlled, is sol-gel conversion which comprises starting from a metal alkoxide and adding a suitable substance to said starting compound to thereby give a structure of a solvent-rich phase that produces macro-pores.

In the method of the present invention, where a water-soluble polymer and a thermally decomposable compound are dissolved in an aqueous acidic solution and a metal compound having a hydrolyzable functional group is added thereto to thereby hydrolyze said metal compound, formed is a gel comprising a solvent-rich phase and a skeleton phase as separated from each other in the capillary with the inner diameter of less than 1 mm. After the product (gel) is solidified and then ripened for a suitable period of time, the wet gel is heated whereby the thermally decomposable compound that has been previously dissolved in the reaction system is thermally decomposed, resulting in the increase in the pH of the solvent that is kept in direct contact with the inner walls of particles constituting the skeleton phase. As a result, the solvent corrodes said inner wall to thereby change the inner surface of said inner wall into a roughened one, whereby the pore-size of said particles is gradually enlarged.

For the gel consisting essentially of silica, the degree of said change in an acidic or neutral region will be very small, but with the increase in the thermolysis to enlarge the basic degree of the aqueous solution, the part constituting each pore is dissolved and re-precipitated to give a more flat part, thereby inducing more active reaction to enlarge the mean pore size.

If the gel has only fine and three-dimensionally restrained pores without having any macro-pores, even its part capable of being dissolved under equilibrated conditions could not produce a dissolved substance capable of being diffused into the external solution, so that the original fine pore structure will remain in the gel to have a relatively large proportion. As opposed to this, if the gel has a solvent rich-phase capable of giving macro-pores, it contains a large amount of only two-dimensionally restrained fine pores, so that the exchange of substances between said solvent-rich phase and the external aqueous solution may be effected well frequently in the gel, resulting in the removal of fine pores with the growth of macro-pores in the gel while preventing the entire pore size distribution of the resulting gel from being broadened.

In the thermolyzing step, it is effective to put the gel in a closed condition in order to make the vapor pressure of the thermally decomposed product saturated and to rapidly make the solvent have a steady pH-value.

Specific examples of the thermally decomposable compound employable herein may include urea, and organic amides such as formamide, N-methylformamide, N,N,-dimethylformamide, acetamide, N-methylacet amide, and N,N-dimethylacetamide. However, as will be mentioned in the Examples to follow hereinunder, the thermally decomposable compound is not limited to these, but may be any one capable of making the solvent basic after its thermolysis, since the pH value of the solvent after the thermolysis is an important factor in the method of the present invention. In addition, those capable of producing a compound having the property of dissolving silica, such as hydrofluoric acid, through thermolysis are also usable in the present invention.

The amount of the thermally decomposable compound to be in the reaction system of the present invention may vary, depending on the type of said compound. For urea, for example, its amount may by from 0.05 to 0.8 g, preferably from 0.1 to 0.7 g, per 10 g of the reaction system. The heating temperature for the thermolysis of urea may fall between 40° C. and 200° C., and, after the thermolysis, the pH of the solvent is preferably from 6.0 to 12.0.

Similarly, thermally-decomposable compounds which generate alternative substance which are capable of dissolve silica, e.g. hydrofluoric acid, can also be used.

After the dissolving and re-precipitating reaction has reached its steady condition, the thermolyzing time for obtaining the corresponding pore structure may vary, depending on the size of the intended macro-pores and the volume of the reaction system being processed. Therefore, it is important to determine the shortest thermolyzing time, over which the pore structure of the gel is no more substantially changed under the processing conditions. For example, where urea is used as the thermally decomposable compound and the thermolyzing temperature falls between 60° C. and 200° C., the thermolyzing temperature falls between 30 days (at 60° C.) to 100 hours (at 200° C.).

From the processed gel, the solvent is evaporated off, whereby the gel is dried to be a dry gel which is coherently attached to the inner wall of the capillary with the inner diameter of less than 1 mm. Since there is a probability that some starting compounds will still remain in the dry gel, the dry gel is thereafter heated at suitable temperatures to thereby further pyrolyze the remaining organic substances. As a result of the heat treatment, the intended porous inorganic material is finally obtained. Generally, the drying is conducted at the temperature between 30 and 80° C. for several to several tens of hours, whereas the heat-treatment is performed in the temperature range between 200 and 800° C.

The porous inorganic materials to be obtained according to the method of the present invention have three-dimensionally networked, open through-pores of from 0.5 to 5 μm in diameter, and fine pores of from 2 to 50 nm in diameter as formed on the inner walls of said through-holes. With the columns of which through-pore diameter of below 0.5 μm, the column pressure becomes exceedingly high. With the columns of which through-pore diameter of above 5 μm, the analytical performance becomes exceedingly low. The preferrable through-pore diameter of said column exists between 0.8 and 4 μm, which can be controlled by the reaction parameters such as starting composition, reaction temperature, pH of the reaction solution, molecular weight of the additive polymers and so forth. With the columns of which mesopore diamater of below 2 nm, the diffusion of solutes within the pores becomes exceedingly slow. With the columns of which mesopore diameter of above 50 nm, the specific surface area becomes exceedingly low and exhibits insufficient separation ability. More preferred diameter of mesopores in said column exists between 7 and 30 nm.

The capillary column of the present invention can be used as a separation medium in liquid chromatograph, gas chromatograph, electrophoresis equipment and solid state extraction apparatus.

In the case that the column of the present invention is used in liquid chromatograph, the system comprise said column, an equipment for loading sample solution to said column, an equipment to pump mobile phase to said column and an equipment for detecting particular constituents in the eluent.

The column of the present invention can be used with its inner surface chemically modified with various kinds of silane coupling agents such as; octadecylsilylating or trimethylsilylating agents and aminopropyltrimethoxysilane. For example, octadecyidimethyl-N,N-diethylaminosilane and 1,1,1,3,3,3-hexamethyldisilazane can be used as octadecylsilylating and trimethylsilylating agents, respectively.

The representative means of pumping system includes that with applied voltage which induces electroosmotic flow and that with compressed gas, but not limitative to these examples. The applied voltage varies with the column diameter, and preferred voltage is between 5 and 50 kV. The pressure of the compressed gas for pumping is between 1 and 50 kg/cm$^2$.

Further control of the linear velocity of the mobile phase is desired, and preferred linear velocity of the mobile phase is between 0.3 and 20 mm/s.

The representative means of loading sample to the column includes that with electroosmotic flow, that with gas compression and that with injection by a micro syringe. The representative means of detecting the eluent includes those with UV-visible absorption spectroscope, fluorescence spectrophotometer, differential refractive-index detector, electrical conduction detector and mass-spectrometric detector, and are not limitative to those examples.

One embodiment of the liquid chromatographic setup of said column comprises that with split flow paths where one of the split paths is set open to atmosphere and the other connected to the column. The ratio of flow split to the column should be controlled by pressure-controlling column or flow-resistant tube at the splitting point. The ratio of flow split to the column is preferrably between 1/10 and 1/10000. The pressure-controlling column can be any column with its diameter being thicker than that of said capillary column. For example, ordinary commercially available $C_{18}$ columns can be used.

In the case that the column of the present invention is used in gas chromatograph, the system comprises said column, an equipment for vaporizing the sample, a carrier gas part to transfer the sample to said column and an equipment for detecting particular constituents in the eluent gas.

The column of the present invention can be used with its inner surface modified with various kinds of reagents depending on the sample compounds. For gaseous samples, molecular sieves and porous stuffings can be used. For fatty hydrocarbons, Apiezon L and methylsilicone oil can be used. For aromatic hydrocarbons, phenyl/methyl silicones can be used. For alcohols and polyalcohols, carbowax (polyethylene glycol) can be used. For carbohydrates cyanosilicone can be used. For carboxylic acids carbowax can be used. For esters of fatty acids cyanosilicone can be used. For aldehydes and ketones, alkylphthalates can be used. For esters and polyethers methylsilicone rubber can be used. For phenols methylsilicone oil can be used. For amines carbowax with pottasium hydroxide can be used. For pharmaceuticals and pesticides phenyl/methyl silicone can be used. For steroids methylsilicone rubber and dexisil can be used. For high boiling point compounds Dexsil (polycarboranylene siloxane) can be used. For multicomponent mixtures carbowax esters can be used. Details related to modifications of the inner surface of sorbents for separating other analytes and the use of such modified sorbents are known in the art.

Detectors for said gas chromatograph are known in the art; among these are heat-conduction detectors, flame ionization detectors, electron capturing detectors. The vaporizing equipment can be a glass tube covered by heaters, and all the other known vaporizing method for gas chromatography can be used. For the introduction of the sample to said column in the gas chromatograph setup, the split methods described above can also be used.

In the case that the column of the present invention is used in electrophoretic equipment, the system comprises said column, an equipment for applying high electrical voltage to the column and an equipment for detecting particular constituents which are electrophoretically separated in the column. The electrophoretic equipment is distinguished from the electro-chromatography which utilizes electroosmotic flow in that the sample compounds are ionized and migrate in the column in the former case and the mobile phase is ionized and make a bulk flow in the latter case. Accordingly, the column used for electrophoresis is filled with buffered solution but no effective flow of the buffered solution occurs inside the column. An equipment for applying voltage should be able to apply voltage high enough to ionize the sample solutes, for example several thousand volts are applied in the case of electrophoretically separating proteins. The detection can be performed with UV-visible absorption spectrometry and fluorescence detectors.

Without further elaboration, it is believed that one skilled in the art can, using the preceding description, utilize the present invention to its fullest extent. The preferred specific embodiments and examples are, therefore, to be construed as merely illustrative, and not limitative to the remainder of the disclosure in any way whatsoever.

The entire disclosures of all applications, patents, and publications cited above and below, and of corresponding application Japanese JP-hei 10-88 627, filed Apr. 01, 1998, are hereby incorporated by reference.

EXAMPLES

Example 1

Analysis with Electroosmotic Flow (1) Column Preparation 0.90 g of polyethylene oxide (Aldrich 85,645-2) and 0.90 g of urea was dissolved in 0.01 mol/l aqueous solution of acetic acid. 4.0 ml of tetramethoxysilane was mixed with the above solution under stirring to promote a hydrolysis reaction. After being stirred for few minutes, the resultant transparent solution was transferred and sealed in a capillary having a diameter of 0.1 mm (100 $\mu$m), and was kept at 40° C., where gelation occurred after about 30 minutes.

The gelled sample was further kept at the same temperature for a few hours for aging, and then heated up to 120° C. and kept at the temperature for 1 hour. The liquid contained in the gel sample showed the pH value of 10.7. The resultant wet gel was then dried at 40° C. for 3 days, and heated with a heating rate of 100° C./h up to 400° C. As a result, a porous material composed of amorphous silica was prepared in a capillary having inner diameter of 0.1 mm.

The electron microscopic observation of the cross section of the capillary column proved that said porous material retained well-defined three-dimentionally interconnected through-pores with their median diamter of 2 $\mu$m (=2000 nm). It was also confirmed by the nitrogen adsorption measurement that the inner walls of said through-pores retained finer pores with their median diameter of 25 nm.

(2) Equipment

The capillary column of effective length of 25 cm obtained by the procedure described above was placed in an electro-chromatograph as shown in FIG. 1. Thiourea was detected with a mobile phase of acetonitrile:tris-buffer HCl 50 mM=80:20 adjusted to pH=8 and with varied applied voltage at 20° C.

In FIG. 1, the part numbered 1 is a capillary column of the present invention, #2 a mobile phase container, #3 a sample container, #4 a mobile phase container, #5 a UV-visible absorption detector, #6 a direct-current power source, and electrodes are inserted into the containers #2–4. In loading the sample, the capillary column #1 and the electrodes were moved into the sample container #3, then 5 kV voltage was applied for 3 seconds.

(3) Results of analysis

Chromatograms of detected thiourea with applied voltages of 15, 25 and 30 kV are shown in FIGS. 2, 3 and 4, respectively. In all these Figures, the absissa denotes elution time and the ordinate the electrical current. The linear mobile phase velocities resulted with 15, 25 and 30 kV were 0.74, 1.6, 2.1 mm/s, respectively. The analytical performance (the number of theoretical plates) was almost constant independent of the linear mobile phase velocity.

Example 2

Analysis with Gas Pressure (1) Column Preparation

The capillary column was prepared as described in Example 1.

(2) Equipment

The capillary column of effective length of 25 cm obtained by the procedure described above was placed in a chromatograph as shown in FIG. 5. Thiourea was detected with a mobile phase of acetonitrile:tris-buffer HCl 50 mM=80:20 adjusted to pH=8 and with varied gas pressures at 20° C.

In FIG. 5, the part numbered 51 is a capillary column of the present invention, #52 a mobile phase container, #53 a sample container, #54 a gas cylinder, #55 a regulating bulb, #56 a UV-visible absorption detector, #57 pressure resistant tubings. In loading the sample, the capillary column #51 and the pressure resistant tubings #57 were moved into the sample container #53, then 1 kg/cm$^2$ pressure was applied for 1 second.

(3) Results of Analysis

Chromatograms of detected thiourea with applied gas pressures of 1, 2 and 3 kg/cm$^2$ are shown in FIGS. 6, 7 and 8, respectively. In all these Figures, the absissa denotes elution time and the ordinate the signal intensity. The linear mobile phase velocities resulted with 1, 2 and 3 kg/cm$^2$ were 0.68, 1.3, 2.1 mm/s, respectively. These results indicate the analysis can be performed even with lower applied pressure.

Example 3

Analysis with Electroosmotic Flow (1) Column Preparation

The capillary column described in Example 1 was derivatized with octadecylsilyl ligands. The octadecylsilylation was performed with 20% octadecyldimethyl-N, N-diethylaminosilane solution in toluene, where the said solution was pressurized at 0.05 kg/cm$^2$ and circulated in the capillary column for 3 hours at 60° C.

(2) Equipment

The capillary column obtained by the procedure described above was placed in an electro-chromatograph as shown in FIG. 1. Alkylbenzenes were detected using a mobile phase of acetonitrile:tris-buffer HCl 50 mM=80:20 adjusted to pH=8 and with varied applied voltages at 20° C.

In loading the sample, the capillary column #1 and the electrodes were moved into the sample container #3, then 5 kV voltage was applied for 3 seconds.

(3) Results of Analysis

Chromatograms of detected alkylbenzenes with applied voltage of 20 and 30 kV are shown in FIGS. 9 and 10, respectively. In all these Figures, the absissa denotes elution time and the ordinate the electrical current. The peaks in the Figures denote alkylbenzenes $C_6H_5C_nH_{2n+1}$ where n=0–5 from shorter elution time. The linear mobile phase velocities resulted with 20 and 30 kV were 0.59, 0.89 mm/s, respectively.

Example 4

Analysis with Gas Pressure (1) Column Preparation

The capillary column was prepared as described in Example 3.

(2) Equipment

The capillary column was placed in a chromatograph as shown in FIG. 5. Alkylbenzenes were detected with a mobile phase of acetonitrile:tris-buffer HCl 50 mM=80:20 adjusted to pH=8 and with varied gas pressures at 20° C.

In loading the sample, the capillary column #51 and the pressure resistant tubings #57 were moved into the sample container #53, then 1 kg/cm² pressure was applied for 1 second.

(3) Results of Analysis

Chromatograms of detected alkylbenzenes with applied gas pressures of 1 and 3 kg/cm² are shown in FIGS. 11 and 12, respectively. In all these Figures, the absissa denotes elution time and the ordinate the signal intensity. The linear mobile phase velocities resulted with 1 and 2 kg/cm² were 1.50 and 2.96 mm/s, respectively. These results indicate the analysis can be performed even with lower applied pressure.

Example 5

Analysis with Split Device (1) Column preparation

The capillary column was prepared as described in Example 1.

(2) Equipment

The capillary column of effective length of 25 cm obtained by the procedure described in Example 1 was placed in a chromatograph as shown in FIG. 13. Alkylbenzenes were detected with a mobile phase of 80% methanol–20% water.

In FIG. 13, the part numbered 31 is a pump for delivering the mobile phase, #32 a T-shaped, connector #33 an injector, #34 and #35 T-shaped, connector #36 a pressure controlling column, #37 a capillary column of the present invention, #38 a UV-visible absorption detector, #39 tubings with a split device. The 10 μm C$_{18}$ column (4.6 mm i.d.×10 mm) was used as a pressure controlling column #36, which gave the split ratio of ca. 1/500. The loading of the sample of 0.2 μl was performed by injection with a microsyringe.

(3) Results of Analysis

Chromatograms of detected alkylbenzenes with mobile phase velocities of 0.1, 0.2, 0.3, 0.4 and 0.5 ml/min are shown in FIGS. 14, 15, 16, 17 and 18, respectively. In all these Figures, the absissa denotes elution time and the ordinate the signal intensity (absorptivity). The linear mobile phase velocities resulted with 0.1, 0.2, 0.3, 0.4 and 0.5 ml/min were 0.55, 1.12, 1.71, 2.26, 2.80 mm/s, respectively.

Effects of Invention

As explained above, the present invention produces porous materials with desired pore size distribution in capillaries with the inner diameter of less than 1 mm. In addition, since the pore structure comprize micrometer-range through-pores and nanometer-range fine pores, the porous materials are applied to separation media such as columns for liquid chromatography which requires no packing operation in manufacturing.

What is claimed is:

1. A capillary column comprising a capillary of which the inner diameter is less than 1000 μm and a continuous porous silica gel which uniformly fills the capillary, said silica gel containing both continuous through pores having diameters ranging from 0.5–5 μm and mesopores having diameters ranging from 2–50 nm.

2. Separating equipment comprising a capillary column according to claim 1.

3. Separating equipment according to claim 2, which is a liquid chromatograph.

4. Separating equipment according to claim 2, which is a gas chromatograph.

5. Separating equipment according to claim 2, which is an electrophoresis equipment.

6. Separating equipment of claim 2, wherein the separating equipment is a liquid chromatograph further comprising a means for sample loading, a means for pumping a mobile phase, and a means for detecting particular constituents in an eluent.

7. Separating equipment of claim 2, wherein the separating equipment is a liquid chromatograph further comprising a means for sample loading, a means for pumping a mobile phase, a means for detecting particular constituents in an eluent, and a split flow comprising at least two paths between said means for sample loading and the column, wherein one of the paths is open to air.

8. Separating equipment of claim 2, wherein the separating equipment is a gas chromatograph, further comprising means for sample vaporization connected to an inlet of the column, means for supplying carrier gas to load the vaporized sample to the column, and means for detecting particular constituents in an eluent which are separated through the column.

9. Separating equipment of claim 2, wherein the separating equipment is an electrophoresis equipment, further comprising means for applying voltage to the column, and means for detecting particular constituents in an eluent which are electrophoretically separated in the column.

10. A capillary column according to claim 1, wherein the silica gel is prepared in situ in the capillary column.

11. A capillary column comprising a capillary of which the inner diameter is less than 1000 μm and a continuous porous silica gel which uniformly fills the capillary, said silica gel having both through pores having diameters ranging from 0.5–5 μm and mesopores having diameters ranging from 2–50 nm, produced by a) forming a three-dimensional co-continuous network containing an inorganic gel phase and a solvent phase both having average domain size of larger than 100 nm via a sol-gel process from a solution precursor containing a thermally decomposable component in a capillary with the inner diameter of less than 1 nm, b) heating resultant wet gel to decompose said thermally decomposable component, whereby nanometer-range microstructures are modified into sharply distributed smaller than 50 nm in diameter, c) drying and heat-treating resultant gel to obtain inorganic porous material.

* * * * *

UNITED STATES PATENT AND TRADEMARK OFFICE
CERTIFICATE OF CORRECTION

PATENT NO. : 6,531,060 B1
DATED : March 11, 2003
INVENTOR(S) : Kazuki Nakanishi et al.

It is certified that error appears in the above-identified patent and that said Letters Patent is hereby corrected as shown below:

Column 10,
Line 57, reads "less than 1 nm," should read -- less than 1 mm, --
Line 61, reads "sharply distributed" should read -- sharply distributed mesopores --

Signed and Sealed this

Eighteenth Day of May, 2004

JON W. DUDAS
*Acting Director of the United States Patent and Trademark Office*